United States Patent
Won et al.

(10) Patent No.: US 8,802,909 B2
(45) Date of Patent: Aug. 12, 2014

(54) METHOD FOR IMPROVING PRODUCTIVITY AND PROCESS STABILITY IN STYRENE MANUFACTURING SYSTEM HAVING MULTIPLE REACTORS CONNECTED IN SERIES

(75) Inventors: Jong-Kuk Won, Daejeon (KR); Hee-Heon Jang, Chungcheongnam-do (KR)

(73) Assignee: Samsung Total Petrochemicals Co., Ltd., Seosan-si, Chungcheongnam-do (KR)

( * ) Notice: Subject to any disclaimer, the term of this patent is extended or adjusted under 35 U.S.C. 154(b) by 89 days.

(21) Appl. No.: 12/982,272

(22) Filed: Dec. 30, 2010

(65) Prior Publication Data
US 2011/0166399 A1    Jul. 7, 2011

(30) Foreign Application Priority Data
Jan. 6, 2010 (KR) .................. 10-2010-0000921

(51) Int. Cl.
*C07C 5/327* (2006.01)
(52) U.S. Cl.
USPC ............................ 585/441; 585/435; 585/440

(58) Field of Classification Search
USPC .......................................... 585/435, 440–445
See application file for complete search history.

(56) References Cited

U.S. PATENT DOCUMENTS

| | | | |
|---|---|---|---|
| 3,100,807 A * | 8/1963 | Hatfield et al. | 585/440 |
| 3,118,006 A * | 1/1964 | Lovett et al. | 585/441 |
| 3,499,051 A * | 3/1970 | Hamanaka et al. | 585/441 |
| 3,515,763 A * | 6/1970 | Uitti | 585/441 |
| 3,660,510 A * | 5/1972 | Kindler et al. | 585/440 |
| 3,755,482 A * | 8/1973 | Castor et al. | 585/441 |
| 3,801,663 A * | 4/1974 | Knox et al. | 585/441 |
| 4,174,270 A * | 11/1979 | Mayes | 208/64 |
| 4,347,396 A * | 8/1982 | Takano et al. | 585/441 |
| 5,053,572 A * | 10/1991 | Kim et al. | 585/441 |
| 7,910,784 B2 * | 3/2011 | Schwint et al. | 585/444 |

* cited by examiner

Primary Examiner — In Suk Bullock
Assistant Examiner — Candace R Chouinard
(74) Attorney, Agent, or Firm — Young & Thompson

(57) ABSTRACT

A method for improving productivity and process stability in styrene monomer manufacturing system using a reaction system having multiple reactors connected in series, which can prevent destruction of the embedded catalyst and bending of a screen which supports catalyst and achieve homogeneous catalyst inactivation during the reaction by divergence of some portions of the feed containing steam and ethylbenzene and injection thereof into a certain point of the system.

4 Claims, 4 Drawing Sheets

METHOD FOR IMPROVING PRODUCTIVITY AND PROCESS STABILITY IN STYRENE MANUFACTURING SYSTEM HAVING MULTIPLE REACTORS CONNECTED IN SERIES

FIELD OF THE INVENTION

The present invention relates to a method for improving productivity and process stability in styrene manufacturing process via catalytic dehydrogenation of ethylbenzene in the presence of steam by enhancing the feeding method of the feed.

BACKGROUND OF THE INVENTION

Styrene, a raw material for major polymer products such as polystyrene, ABS, SBR and the like, is consumed at more than 30 million tons per year worldwide with an increasing demand at a rate of up to 3%, thereby being one of the representative general-purpose monomer products.

It is well-known in the field of chemistry that styrene can be prepared by dehydrogenating ethylbenzene in the presence of overheated water vapor, i.e., steam on a dehydrogenation catalyst bed in a reactor. Such a styrene preparation process is an endothermic reaction that occurs under a high temperature condition, and thus is regarded to be one of the representative great energy-consuming processes. As for the heat source for the reaction, ultrahigh temperature steam is used, where the steam does not participate in the reaction, but just passes through the reactor. The steam is separated from the products and collected as condensed water from the process by recovering the waste heat and then cooling with cooling water. In the above process, the amount of heat corresponding to latent heat when the steam is condensed to water is lost.

In such dehydrogenation process, a high conversion rate of ethylbenzene and high selectivity to styrene which inhibits the generation of side products such as benzene and toluene is considered to be important. In the process, process parameters affecting to dehydrogenation performance may include reaction temperature, reaction pressure, space velocity, a mixing ratio of steam and the like.

Since the dehydrogenation reaction of ethylbenzene is an endothermic reaction, the higher the reaction temperature, the more the reaction is advantageous. However, when the reaction temperature is excessively high, the selectivity to styrene decreases, and a side-reaction which generates benzene, toluene or the like becomes dominant. Due to rather great amount of reaction heat, the outlet temperature of a reactor is significantly lower than the inlet temperature of the reactor. For compensating the temperature difference, the conventional dehydrogenation process employs multiple reactors, and energy equivalent to the amount lost as reaction heat is provided to the reactors.

Related to this, Korean patent application No. 1998-042067 and U.S. Pat. No. 5,856,605 disclose a method for minimizing heat loss as reaction heat by heating the exterior surface of multiple tube reactors filled with catalyst, by using a heat-transfer medium. U.S. Pat. No. 5,358,698 discloses a method for improving the flowability of the fluid and thus the reactor performance, by attaching a baffle with a specific shape inside the reactor.

SHR (Steam to Hydrocarbon Ratio) is defined as a molar ratio of steam to aromatic compounds introduced to a reactor.

In most reactions, water acts as a catalytic poison, however it is well-known that it plays important roles in the dehydrogenation of ethylbenzene. It is known that steam reacts with K and Fe, generates active sites, supplies latent heat to the endothermic reaction of ethylbenzene, and thus removes deposited carbon. Since it needs lots of energy to maintain steam at the temperature more than 600° C., a process using the minimum amount of energy is preferred. When an excessive amount of steam is used at high temperature, an important active component of a dehydrogenation catalyst, i.e., K (potassium) is dissolved and eluted through a reactor outlet. Such an event has been indicated as a main reason for deactivation of the catalyst [Applied Catalysis A: General 212 (2001) 239].

In this circumstance, current studies have been more focused on the development of a catalyst which can maintain high activity under relatively low temperature steam conditions. Korean patent laid-open No. 2001-0028267 and Korean patent laid-open No. 2001-0028268 disclose a method for preventing a decrease in catalyst activity caused by the loss of K, by artificially injecting KOH into a reactor.

Since the number of the resulting product molecules are more than that of the reactants, the conversion rate in the ethylbenzene dehydrogenation becomes lower as the pressure increases. Therefore, it is desired to operate the process under as low a pressure as possible, however without imparting too much load to the capacity of a compressor. When the pressure is lowered, stability is increased due to a decrease in catalyst coking, and also selectivity to the main product is improved owing to the relatively decreased side-reaction. Consequently, it is considered that pressure reduction is very advantageous in the process.

Korean patent application No. 1990-0017968 and U.S. Pat. No. 5,053,572 describe a multistage ethylbenzene dehydrogenation process in which a fraction of ethylbenzene is fed to a first reactor and the remaining fraction of ethylbenzene together with a product of the first reactor is fed to a second reactor in multistage ethylbenzene dehydrogenation process. The intended effect of divergence of ethylbenzene or steam in these prior arts relates to: improvement in the ethylbenzene conversion rate owing to the modification of the mixing temperature and composition of the ethylbenzene and steam; increase in selectivity to styrene; and extended catalyst life due to prevention of coking generation. In other words, these prior arts do not disclose the effect of productivity and process stability as it is intended in the present invention, by making in improvement related to the position of injecting the feed containing steam and ethylbenzene.

FIG. 3 shows an adiabatic reactor conventionally used in styrene manufacturing, in which the catalyst bed has a cylindrical shape and is supported by a screen. The adiabatic reactor may be used connected in series. When the more reactors are connected in the system, an increased flow rate of the feed is required. To increase in the flow rate of the feed, the catalyst bed should be thinner while the contact area should be increased to reduce the linear velocity of gas and the fluidization of catalyst particles. However, once a reactor is established and arranged in a system, it is nearly impossible to reconstruct the shape of the reactor, and replacement with a new reactor disadvantageously requires great expense.

Moreover, most styrene manufacturing plants currently in operation in the world use a reaction system having 2 to 3 adiabatic reactors connected in series, wherein the reaction system further comprises, as shown in FIG. 1, furnaces and heat exchangers, which makes it difficult to connect additional pipe for ultrahigh temperature use and thus extend the system by adding further reactors. Therefore, in the case of extending a reaction system having two adiabatic reactors connected in series, it is generally known to simply add one additional reactor having greater capacity than that of the existing reactors downstream of the system, after the two existing reactors. This reactor to be added usually has a volume 2-5 times greater than that of the existing two reactors in order to get the most from the extension of the system, i.e., to maximize the productivity. However, in that case, the reactor capacity will be significantly out of the optimal system design at the time of system construction. Further, the increased flow rate will be excessive to the existing two reactors, which were designed suitably for a system having two reactors in series. This will cause fracture of catalysts due to fluidization of catalyst particles as well as uneven deactivation of catalysts due to the difference in the amount of catalyst filling the reactor.

In this respect, no method has been found that uses a divergence of feed material before the present invention, in order to solve the problems occurred when extending a system by adding a reactor so as to improve productivity. Further, it is difficult to specifically select the optimal injection point of a feed material to the system, since a conventional styrene monomer manufacturing system as shown in FIG. 1 is composed of a complex heat exchanging network which includes furnaces and heat exchangers for heat supply and waste heat recovery.

In the meantime, the major operational hindrance in the styrene manufacturing reaction system is the temperature of ultrahigh temperature steam discharged from the furnaces (F-1, F-2 and F-3), which is also referred as Hot-Piping Temperature (HPT). HPT is usually limited to a range of 800-900° C. When the operation temperature is out of this range, the operation is automatically halted, and the temperature range is called an interlock temperature. The temperature range has been determined as above, based on the generation of cracks at the junction part owing to material or thermal stress of a heat exchanger and a pipe through which ultrahigh temperature steam passes. Therefore, the temperature range may vary depending on the material and design of the equipment used in the system. In operation, it is important to decrease the temperature as much as possible. However, with the elapse of time, a reactor filed with catalysts becomes deactivated, which requires the increase in reaction temperature, and thus the temperature is accordingly increased. Therefore, it is important to maintain the temperature as low as possible so as to avoid the temperature going over the limited range at the time of halting the operation due to the end of catalyst life. Moreover, by lowering the temperature, the life of equipment used in the system may be advantageously extended.

SUMMARY OF THE INVENTION

The object of the present invention is to provide a method for preparing styrene monomers using a reaction system having multiple reactors connected in series, which can prevent destruction of the embedded catalyst and bending of a screen which supports catalyst and achieve homogeneous catalyst inactivation during the reaction, thereby ultimately improving the productivity of styrene monomers and process stability, by divergence of some portions of the feed containing steam and ethylbenzene and injection thereof into a certain point of the system.

DETAILED DESCRIPTION OF THE INVENTION

The method for improving productivity and process stability in a styrene preparation process system using multiple reactors connected in series according to the present invention, is characterized in that the feed containing steam and ethylbenzene, and ultrahigh temperature steam diverge and then are separately injected into a point after an adiabatic reactor of the front part of the system or a point before an adiabatic reactor of the rear part of the system.

In the styrene monomer manufacturing system according to the present invention, the additional adiabatic reactor at the rear part of the system generally has a volume 2-5 times greater than that of the adiabatic reactor of the front part of the system, in order to maximize the productivity.

In the styrene monomer manufacturing system according to the present invention, 15-20 vol % of the feed containing ethylbenzene and steam, based on the total amount of being fed to the reaction system, diverge.

In the styrene monomer manufacturing system according to the present invention, 15-20 vol % of the ultrahigh temperature steam, based on the total amount of being fed to the reaction system, diverge.

The flow rate for divergence of the feed is not specifically limited, however the degree of effect obtained may be varied according to an increase or decrease in the flow rate of divergence. Further, in view of the prevention of fluidization of catalyst particles filled in an adiabatic reactor and the reactor capacity, the range of 15-20 vol % is preferred.

The method for improving productivity and process stability in styrene manufacturing process according to the present invention is further illustrated with reference to the drawings.

Hereinafter, the present invention is illustrated in detail with an embodiment of a conventional reaction system wherein 3 reactors are connected in series after extension of the system in view of the cost-effectiveness of the reaction system, as shown in the attached drawings, however the system illustrated in the drawings is only a preferred example of the present invention, and does not limit the scope of the present invention. Therefore, the present invention may be applied to any systems having multiple reactors connected in series without being limited to the system having 3 reactors connected in series.

One embodiment of the method for improving productivity and process stability in a styrene manufacturing system having multiple adiabatic reactors connected in series according to the present invention is disclosed in FIGS. 2a-2e, in which divergence and injection of the feed material in a conventional styrene manufacturing system as shown in FIG. 1 are carried out at the point as indicated in FIGS. 2a-2e so as to manufacture styrene monomers.

FIG. 1 shows a conventional styrene manufacturing system in which two adiabatic reactors R-1 and R-2 are connected in series and an additional reactor R-3 which has a volume 2-5 times greater than that of R-1 and R-2 is further added to the rear part of the system, without any divergence of the feed.

In FIG. 1, the feed containing ethylbenzene and steam is fed to the heat exchanger HX-3 at 200-250° C., and vaporized in HX-3 as a gas having a temperature of about 400-500° C. The feed with an elevated temperature is mixed with ultrahigh temperature steam heated in the furnace F-1, resulting in further temperature elevation to about 600-650, and then injected to the reactor R-1. Since the styrene manufacturing process is a great endothermic reaction, the temperature of the reactants is dropped to around 540-590° C. as passing through the reactor R-1. The temperature of the reactants discharged from the reactor R-1 is elevated to about 600-650° C. in HX-1 through heat exchange with ultrahigh temperature steam heated in the furnace F-2, and injected into the reactor R-2. Based on the same principle, the temperature of the reactants discharged from the reactor R-2 is again elevated to about 600-650° C. in HX-2 through heat exchange with the ultrahigh temperature steam heated in the furnace F-3, and injected to the reactor R-3, finally resulting in a hot styrene product having a temperature of about 540~590° C. The hot styrene product is subjected to heat exchange with the feed containing ethylbenzene and steam in HX-3, and thus the temperature drops to around 350-400° C.

The raw materials, i.e. ethylbenzene and steam fed to HX-3, as shown in FIGS. 2a-2e which show the improved process according to the present invention, may diverge at the point A or point B. The amount (flow rate) of divergence is 15-20 vol % of the total amount of the raw materials fed to the system. The ultrahigh temperature steam obtained from the furnace F-2 may diverge at the point C, D or E, and the divergence amount thereof is 15-20 vol % of the total amount of steam fed to the furnace F-2. The diverged feed containing ethylbenzene and steam, and the diverged ultrahigh temperature steam are mixed together and injected at the point P (after the reactor of the front part of the system) or the point Q (before the reactor of the rear part of the system) into the reaction system. Although the divergence of the feed containing ethylbenzene and steam may be carried out at the point A or B, the point A is preferred.

Since the temperature at the point B (around 150-250° C.) is around 300-350° C. lower than the temperature at the point A (around 450~550° C.), when using the point B, HPT of F-3 is significantly increased to around 200-230° C.

The divergence amount of the feed is not specifically limited according to the present invention, however the degree of effect obtained may be varied according to an increase or decrease in the divergence amount. However, when the flow rate fed to the reactor R-1 is reduced by 15-20 vol %, fluidization of catalyst particles may be significantly reduced in R-1 and R-2 reactors which have a small capacity as well as the inner wall surface area, therefore the above range is preferably used. In the meantime, in the reactor R-3, which has greater capacity than the reactor R-1 or R-2, as well as greater inner all surface area, the fluidization of catalyst particles related with the total flow rate is not a big problem.

The divergence of ultrahigh temperature steam discharged from the furnaces (F-1, F-2 and F-3) may be carried out at the point C, D or E. Assuming the effect is constant, the point C only directly affects HPT of F-1; the point D directly affects HPT of F-1 and F-3; and the point E directly affects HPT of F-1, F-2 and F-3. Therefore, the point C is the best for the divergence point. In the above, the expression 'directly affects' means a reduction in heat supply or heat exchange capability due to reduction in the flow rate caused by the divergence. Such reduced capability results in direct increase in HPT.

The ratio of each divergence amount of the ultrahigh temperature steam and the feed containing ethylbenezene and steam is not specifically limited, however for maintaining the suitable catalyst activity and preventing the polymerization of the resulted product styrene monomers, the same ratio, for example 15-20 vol % may be used.

The diverged feed containing ethylbenzene and steam and the diverged ultrahigh temperature steam may be injected at the point P or point Q into the reaction system as shown in FIGS. 2a-2e. At this time, the diverged ultrahigh temperature steam and the diverged feed containing ethylbenzene and steam should be mixed together and injected at one point of the system. When they are injected separately to other points of the system, significant change in Steam hydrocarbon ratio (SHR), i.e. the ratio between the amount of steam and hydrocarbon occurs, which may cause styrene polymerization, resulting in decrease in selectivity, and further steam and hydrocarbon may not be suitably mixed together.

Since injection at the point Q have a small influence on HPT of the furnaces (F-1, F-2 and F-3), it is preferred as compared to the injection at the point P. However, when the HPT of F-3 is sufficiently lower, for example more than 30° C., than the limitation temperature, i.e. interlock temperature, the point P may be used. In this case, the selection of the point P or Q may be determined by workability in view of space, position or material of the system.

FIG. 3 shows the structure of an adiabatic reactor used in a styrene manufacturing system. FIG. 4 shows the catalyst bed inside the adiabatic reactor of FIG. 3, wherein the catalyst bed is charged inside the adiabatic reactor in the form of a cylinder and supported by a metal screen in the form of a net.

As shown in FIG. 3, reactants for the styrene manufacture flow into the bottom of the adiabatic reactor, pass inside the reactor contacting and reacting with the inner wall of the catalyst bed, and are discharged to the top of the reactor. As the gas flow passes by the inner wall of the catalyst bed at a high speed, it pressurizes the catalyst bed and the screen. When the pressure is more than a certain degree, fluidization of catalyst particles occurs, which causes abrasion and destruction of the catalyst particles, resulting in a decrease in catalyst performance. Further, the pressure gradient is increased in the catalyst bed, leading to a further increase in the load to the compressor at the end part. The resulting increase in overall reaction pressure consequently has disadvantageous effects on the reaction system. Moreover, the pressure applied to the catalyst bed also affects the screen, causing bending thereof and thus decrease in the life of the catalyst bed.

Since the pressure applied to the catalyst bed is in proportion with the linear velocity of fluid, it is necessary to reduce the linear velocity of fluid, which can be achieved by reducing the amount fed to the system or increasing the inner side wall area of the catalyst bed as shown in FIG. 4. Since it is not possible to modify the catalyst bed once filled in a reactor, the only possible effective method for reducing the pressure by adjusting the operation condition may be a reduction of the amount fed to the system. However, by installing an additional reactor in order to increase productivity, an increase in the total flow rate occurs which may cause problems such as decrease in catalyst performance, increase in reaction pressure and screen bending.

Moreover, when the amount of ethylbenzene fed to the reactor is increased, the reaction performance, i.e. the ethylbenzene conversion rate is accordingly decreased. Therefore, changes in the styrene production amount which is estimated by the equation (flow rate of ethylbenzene)×(conversion rate) should be taken into consideration.

According to the method of the present invention, it is possible to prevent problems such as decrease in catalyst performance, increase in reaction pressure and bending of a screen, thereby significantly improving productivity and process stability in styrene monomer manufacturing system, in spite of increase in flow rate of the feed and steam according to further establishment of a reactor, by divergence of the feed and steam fed to the system and injection thereof again into the system.

BRIEF DESCRIPTION OF THE DRAWINGS

In the figures, each point A and point B is a point where the raw material ethylbenzene and steam may diverge; each point C, point D and point E is a point where the ultrahigh temperature steam discharged from the furnace may diverge; and each point P and point Q is a point where the raw materials and the ultrahigh temperature steam diverged above may be injected. FIG. 2a shows divergence at the point A and point C and then injection at the point Q; FIG. 2b shows divergence at the point B and point C and then injection at the point Q; FIG. 2c shows divergence at the point A and point C and then injection at the point P; FIG. 2d show based on the total amount of being fed to the reaction systems divergence at the point A and the point E and then injection at the point Q; FIG. 2e shows divergence at the point A and point D and then injection at the point Q.

DETAILED DESCRIPTION OF THE INVENTION

Hereinafter, the effect of the present invention is illustrated through the following examples.

In all of the following examples, the amount of divergence and the amount of styrene produced are constantly maintained, thus only fact to be considered is HPT.

Although a problem related with fluidization of catalyst particles is improved and a problem related with HPT do not occur according to the method of the present invention which includes divergence of the feed and injection thereof at a certain point of the system, it cannot be regarded to be significant if the method involves a decrease in production amount. Therefore, comparison of the effects between the examples should be made on the premise of the same production amount and thus the examples are estimated based on the same amount of divergence and production.

Since such estimation of the production amount cannot be tested in the real plant, a simulator ($1^{st}$ principle model) was used for the estimation in the present examples. Further, HPT value was also obtained by the simulator. The estimation obtained by the simulator was made by adjusting parameters according to operation data practiced in the real plant, and thus had superior precision in estimation.

For obtaining the constant production amount of styrene with a given amount of divergence, the inlet temperature of a reactor should be modified so as to further modify the reaction performance, i.e. the conversion rate of ethylbenzene. For this purpose of obtaining the constant production amount of styrene, only the inlet temperature of the reactor R-3 was modified in the following examples. The modification in inlet temperature of R-3 directly affects to HPT of F-3, after all. Therefore, the temperature change in HPT may be a proper indicator reflecting the effects of the divergence and injection of the feed according to the present invention, in which the effects related to energy balance as well as reaction performance.

In the examples, the reactor R-3 is selected only because of its greater volume, and although other reactor is selected for changing the conversion rate, the same tendency in results is expected. General operation conditions used in conventional styrene manufacturing plant were used.

Experiment Example 1

Divergence of the Feed and Ultrahigh Temperature Steam

Figure 1:
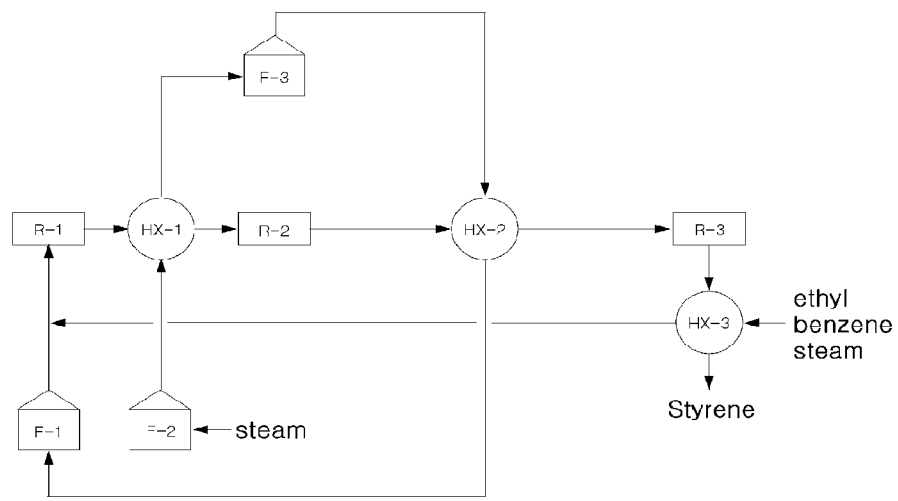
FIG. 1 schematically represents a reaction system of a conventional styrene manufacturing process in which 3 adiabatic reactors are connected in series, in which each R-1, R-2 and R-3 is an adiabatic reactor; each HX-1, HX-2 and HX-3 is a heat exchanger; F-1, F-2 and F-3 is a furnace.
Figure 2A:
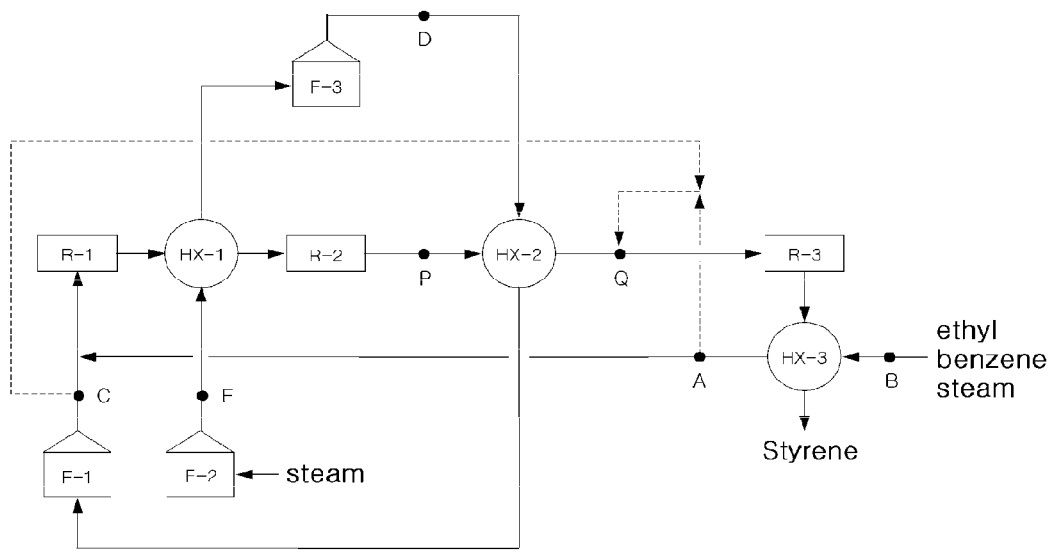
FIGS. 2a-2e show improved styrene manufacturing process proposed by the present invention, wherein the dotted lines represent the portion modified by the present invention.
Figure 2B:
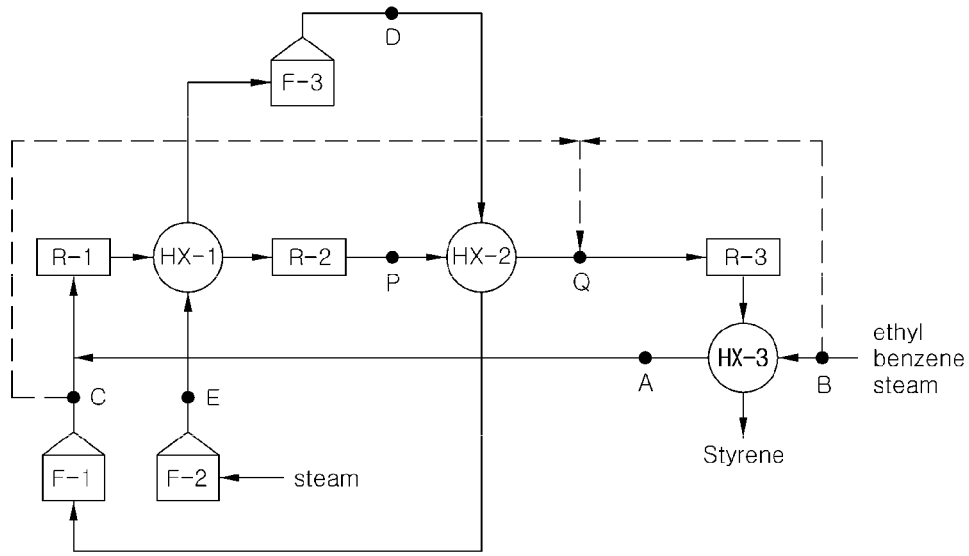
Figure 2C:
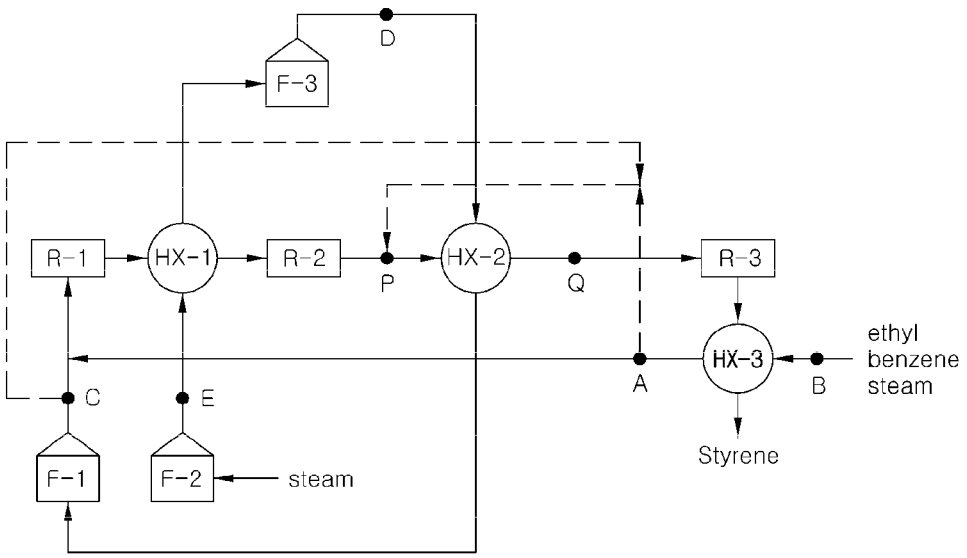
Figure 2D:
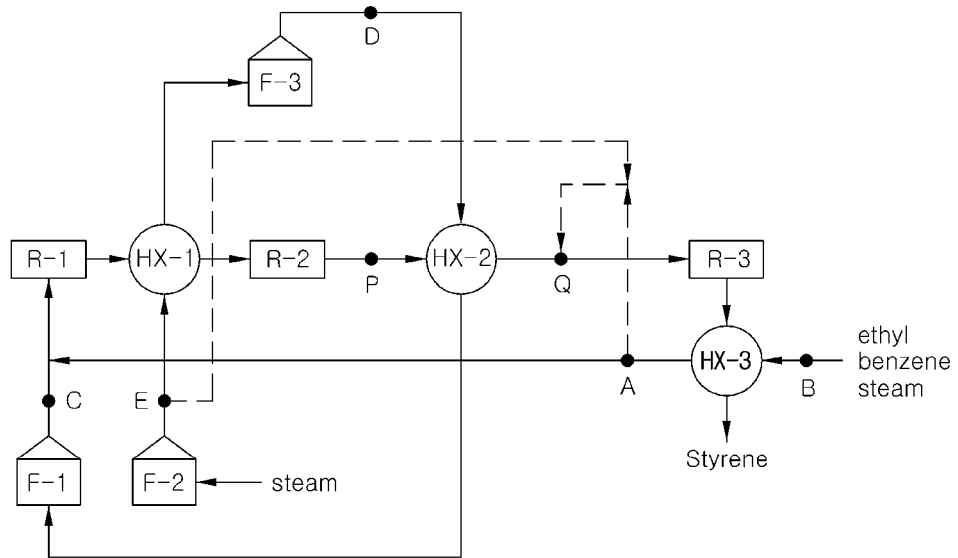
Figure 2E:
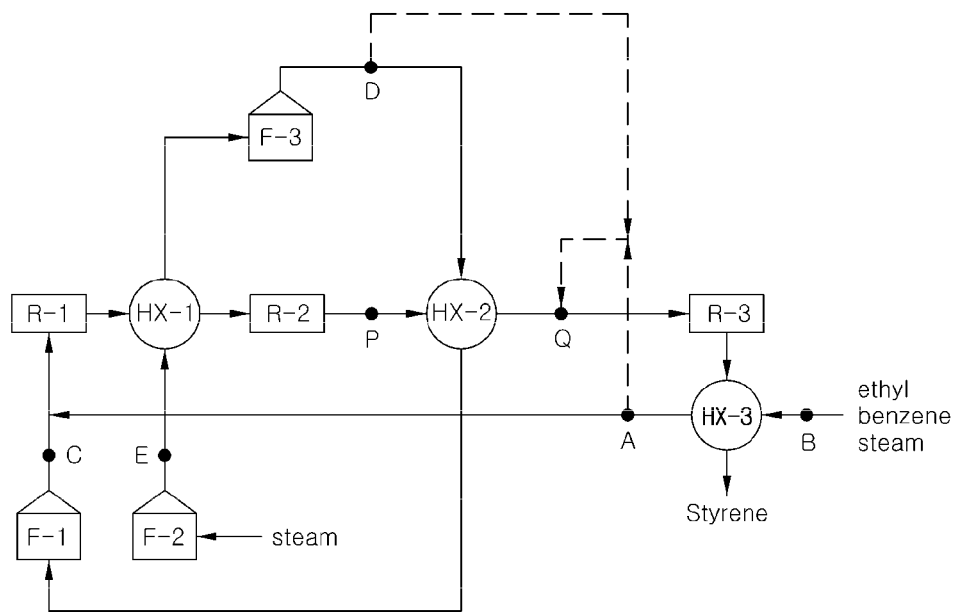
Figure 3:
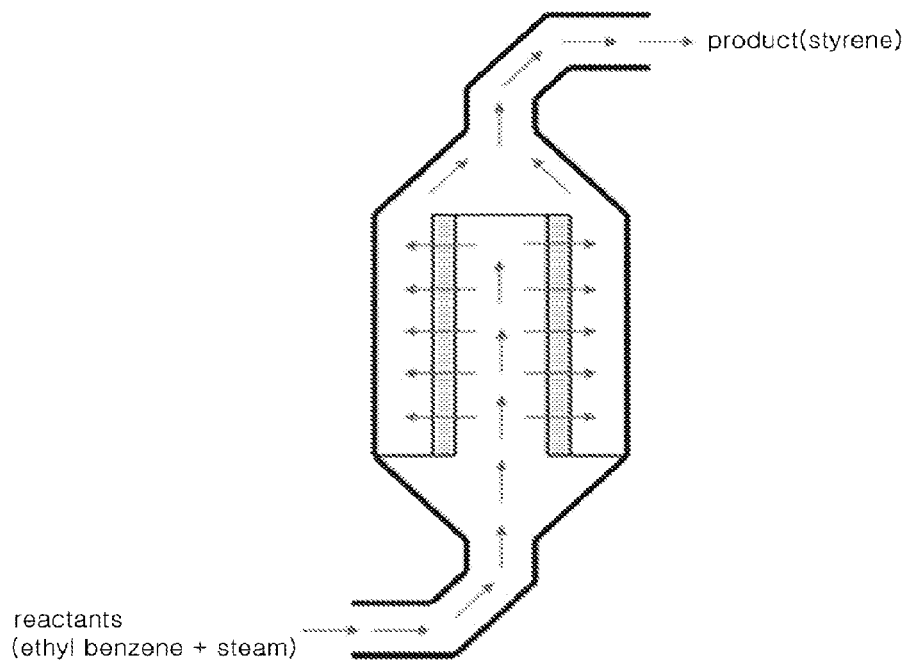
FIG. 3 shows an adiabatic reactor conventionally used in styrene manufacturing, together with the stream of reactants flowing to the direction of the arrows. The shaded rectangles inside the reactor represent the catalyst beds which are filled in a screen having a cylindrical form.
Figure 4:
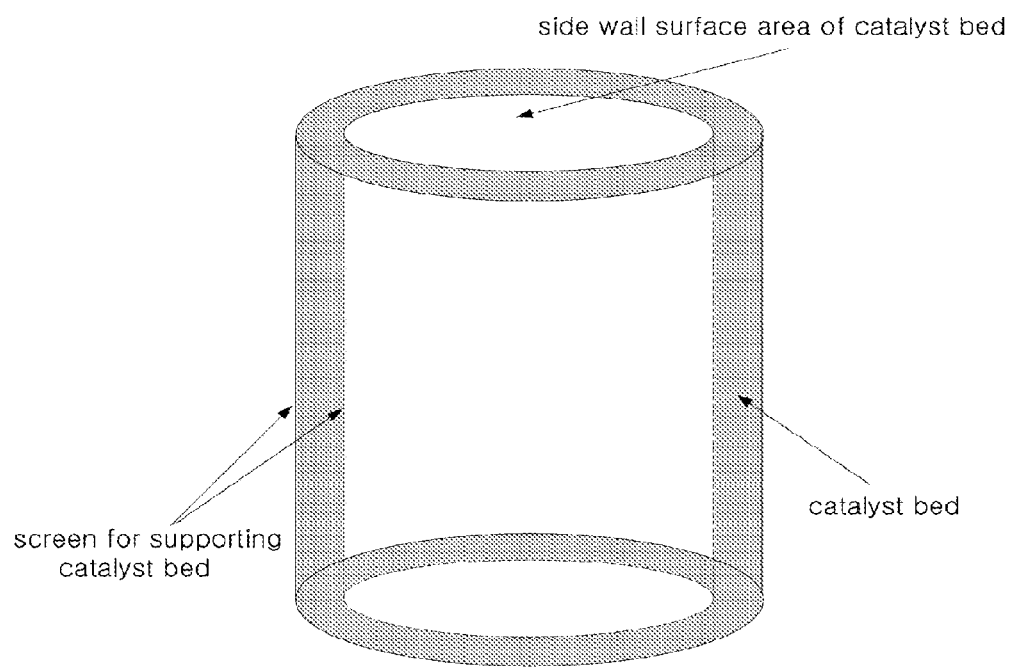
FIG. 4 shows the structure of the catalyst bed constructed in the form of a cylinder. The inner wall surface area of the catalyst bed is the surface of the wall inside the cylinder which contacts with the reactants fed into the reactor.

The feed containing ethylbenzene and steam diverged at the point A and the amount thereof was 17.0 vol % of the total amount of the feed being fed. The ultrahigh temperature steam was possible to diverge at the point C, D or E as shown in FIGS. 2a-2b, with the amount of 17.0 vol %.

The divergence at the point C is considered to be most advantageous in theory, since the point C directly affects HPT of F-1 with same degree of effect, although the point D directly affects HPT of F-1 and F-3, and the point E directly affects HPT of F-1, F-2 and F-3. In the above, the 'directly affects' means reduction in heat supply or heat exchange capability due to reduction in the feed amount caused by the divergence. Such reduced capability results in direct increase in HPT. The tendency and the degree of temperature change was estimated and compared through simulation.

The case 1 in which only ultrahigh temperature steam diverged at the amount of 17 vol %, and the case 2 in which the feed containing ethylbenzene and steam diverged at the amount of 17 vol % were analyzed, in which the changes in HPT of F-1, F-2 and F-3 according to 3 different point of divergence were shown in the following Table 1.

TABLE 1

| Case | Divergence point | Changes in HPT (° C.) | | |
|---|---|---|---|---|
| | | F-1 | F-2 | F-3 |
| Case 1 | C | (+) 26.7 | (−) 2.9 | (−) 29.0 |
| | D | (+) 26.7 | (−) 2.9 | (+) 3.0 |
| | E | (+) 26.7 | (+) 30.9 | (−) 11.6 |
| Case 2 | C | (+) 30.1 | (−) 30.1 | (−) 18.2 |
| | D | (+) 30.1 | (−) 30.1 | (+) 12.8 |
| | E | (+) 30.1 | (−) 2.3 | (+) 7.3 |

As seen from the simulation results of the above Table 1, although the 3 different divergence points did not showed big difference in the effects on HPT of F-1, the point C showed the least effect on HPT of F-2 and F-3. Therefore, it was confirmed that the point C was the optimal position for divergence of ultrahigh temperature steam.

Experiment Example 2

Injection of the Diverged Amount of the Feed and Ultrahigh Temperature Steam

The point P or point Q in FIGS. 2a-2e is the point for possibly injecting the ultrahigh temperature steam, and the raw materials, i.e. ethylbenzene and steam diverged.

It is difficult to determine which point between the point P and point Q is more advantageous, theoretically. For selecting the more preferred injection point, the different effects of the injection point P and point Q on HPT of F-1, F-2 and F-3 (i.e., by the equation of (HPT at the position P-HPT at the position Q)) were simulated and compared, with a given divergence point of the point C for ultrahigh temperature steam. The results were summarized in the following Table 2.

TABLE 2

| | Furnace | | |
|---|---|---|---|
| | F-1 | F-2 | F-3 |
| (HPT at the position P - HPT at the position Q) ° C. | 0.0 | 0.0 | 4.0 |

From the results of Table 2, although the injection point of the point P or point Q only had small influence on HPT of F-3, the point Q was more preferred.

However, as seen from the above Table 2, since just small difference in HPT of F-3 is present, it can be determined that the divergence point has more influence than the injection point, and since the difference between the point P and point Q is not so much, the point P may be used, when HPT of F-3 is sufficiently low as compared to the interlock temperature of the system.

INDUSTRIAL AVAILABILITY

According to the present invention, it is possible to improve productivity and process stability in styrene monomer manufacturing system having multiple reactors connected in series due to the improved method including divergence of the feed and injection thereof to the reaction system. The method according to the present invention is particularly effective when the reactors in the latter part of the system have larger volume than the reactors in the front part of the system.

What is claimed is:

1. A method for improving productivity and process stability in a styrene preparation process system comprising:

Providing first (R-1), second (R-2), and third (R-3) adiabatic reactors connected in series, the first adiabatic reactor (R-1) having a first heat exchanger (HX-1) located downstream and a first furnace (F-1) located upstream, the second adiabatic reactor (R-2) having a second heat exchanger (HX-2) located downstream and a second furnace (F-2) located upstream, and the third adiabatic reactor (R-3) having a third heat exchanger (HX-3) located downstream and a third furnace (F-3) located upstream;

diverging a portion of a raw material containing steam and ethylbenzene downstream from the third heat exchanger (HX-3) to produce a diverged raw material;

diverging a portion of a steam having a temperature in the range of 800-900° C. discharged from the first furnace (F-1) to produce a diverged steam;

mixing the diverged raw material and the diverged steam to produce a first mixture; and injecting the first mixture at a point (P) downstream from the second adiabatic reactor (R-2) and upstream from the second heat exchanger (HX-2) or injecting the first mixture at a point (Q) downstream from the second heat exchanger (HX-2) and upstream from the third adiabatic reactor (R-3).

2. The method according to claim 1, wherein the third adiabatic reactor (R-3) has a volume 2-5 times greater than each of the first (R-1) and second (R-2) adiabatic reactors.

3. The method according to claim 1, wherein the diverged raw material is 15-20 vol % of a total amount of the raw material containing the ethylbenzene and the steam.

4. The method according to claim 1, wherein the diverged steam is 15-20 vol % of a total amount of the steam feed.

* * * * *